(12) United States Patent
Fujikado et al.

(10) Patent No.: US 7,398,124 B2
(45) Date of Patent: Jul. 8, 2008

(54) VISUAL RESTORATION AIDING DEVICE

(75) Inventors: Takashi Fujikado, Toyonaka (JP); Yasuo Tano, Kobe (JP); Yutaka Fukuda, Toyonaka (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 10/624,686

(22) Filed: Jul. 23, 2003

(65) Prior Publication Data

US 2004/0127957 A1   Jul. 1, 2004

(30) Foreign Application Priority Data

Jul. 31, 2002 (JP) .............................. 2002-222360

(51) Int. Cl.
*A61N 1/00* (2006.01)
(52) U.S. Cl. .......................................... 607/54; 607/53
(58) Field of Classification Search ............... 607/53–54
See application file for complete search history.

(56) References Cited

U.S. PATENT DOCUMENTS

| | | | |
|---|---|---|---|
| 2,760,483 A | 8/1956 | Tassicker | |
| 6,393,327 B1 | 5/2002 | Scribner | |
| 6,427,087 B1 | 7/2002 | Chow et al. | |
| 7,003,355 B1 * | 2/2006 | Suaning et al. | ............... 607/54 |
| 2002/0095193 A1 | 7/2002 | Ok et al. | |

FOREIGN PATENT DOCUMENTS

| | | |
|---|---|---|
| JP | A 8-511697 | 12/1996 |
| JP | A 11-506662 | 6/1999 |
| JP | A 2002-505910 A | 2/2002 |
| WO | WO94/26209 | 11/1994 |
| WO | WO96/39221 | 12/1996 |
| WO | WO99/45870 | 9/1999 |
| WO | WO 00/56393 | 9/2000 |

OTHER PUBLICATIONS

Wlater, Peter et al. "Evoked cortical potentials after electrical stimulation of the inner retina in rabbits," *Graefe's Archive For Clinical and Experimental Opthalmology* vol. 238, No. 4, pp. 315-318 Apr. 2000.
R. Rodieck, "The First Steps in Seeing," *Sinauer Associates, Inc.*, pp. 29, 1998.
E. Zrenner "Will Retinal Implants Restore Vision," *Science*, vol. 295, pp. 1022-1025, Feb. 8, 2002.

* cited by examiner

*Primary Examiner*—Mark W Bockelman
(74) *Attorney, Agent, or Firm*—Oliff & Berridge, PLC (57) ABSTRACT

A visual restoration aiding device includes an electrode array (21) having a plurality of electrodes (21*a*) placed on an outside of a choroid (E2) of a patient's eye (E) to electrically stimulate cells constituting a retina (E3).

2 Claims, 7 Drawing Sheets

VISUAL RESTORATION AIDING DEVICE

BACKGROUND OF THE INVENTION

1. Field of the Invention

The present invention relates to a visual restoration aiding device.

2. Description of Related Art

In diseases such as retinitis pigmentosa and age-related macular degeneration (ARMD), retinal photoreceptor cells, which are one type of the cells constituting retina, get denatured and deaden, gradually decreasing visual acuity of patients and then causing vision loss as the diseases progress. At present, there is no effective treatment for such diseases. For this purse, there have been conducted the researches to assist visual restoration by transmitting electrical stimulation pulses to an electrode array placed on the inside or outside of the retina, thereby electrically stimulating the cells constituting retina, such as bipolar cells, retinal ganglion cells, and others.

In this case where the electrode array is placed on the inside or outside of the retina, the size of the electrode array is required to be smaller in order to minimize damage to the retina, However, a visual field obtained during the visual restoration becomes narrower as a smaller electrode array is used. Furthermore, such case needs a high operating technique and there is the fear of damage to the retina by the operation.

SUMMARY OF THE INVENTION

The present invention has been made in view of the above circumstances and has an object to overcome the above problems and to provide a visual restoration aiding device capable of effectively restoring vision while preventing a retina from being damaged due to placement of an electrode array.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a visual restoration aiding device including: an electrode array having a plurality of electrodes placed on an outside of a choroid of a patient's eye to electrically stimulate cells constituting a retina.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
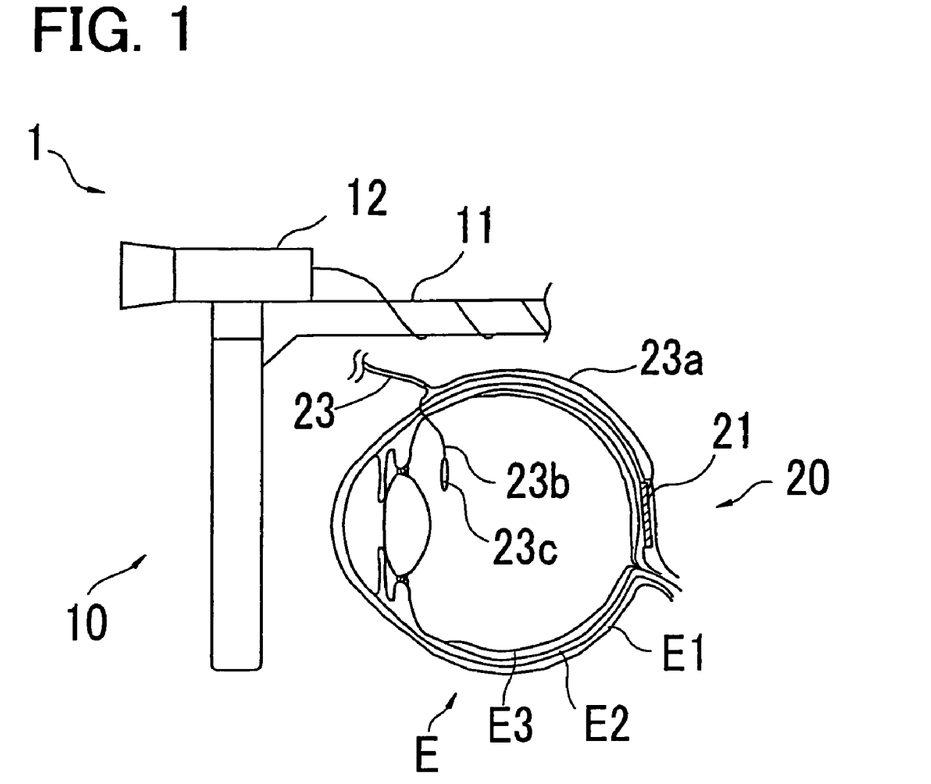
FIG. 1 is a schematic structural view of a visual restoration aiding device in an embodiment according to the present invention.
Figure 2:
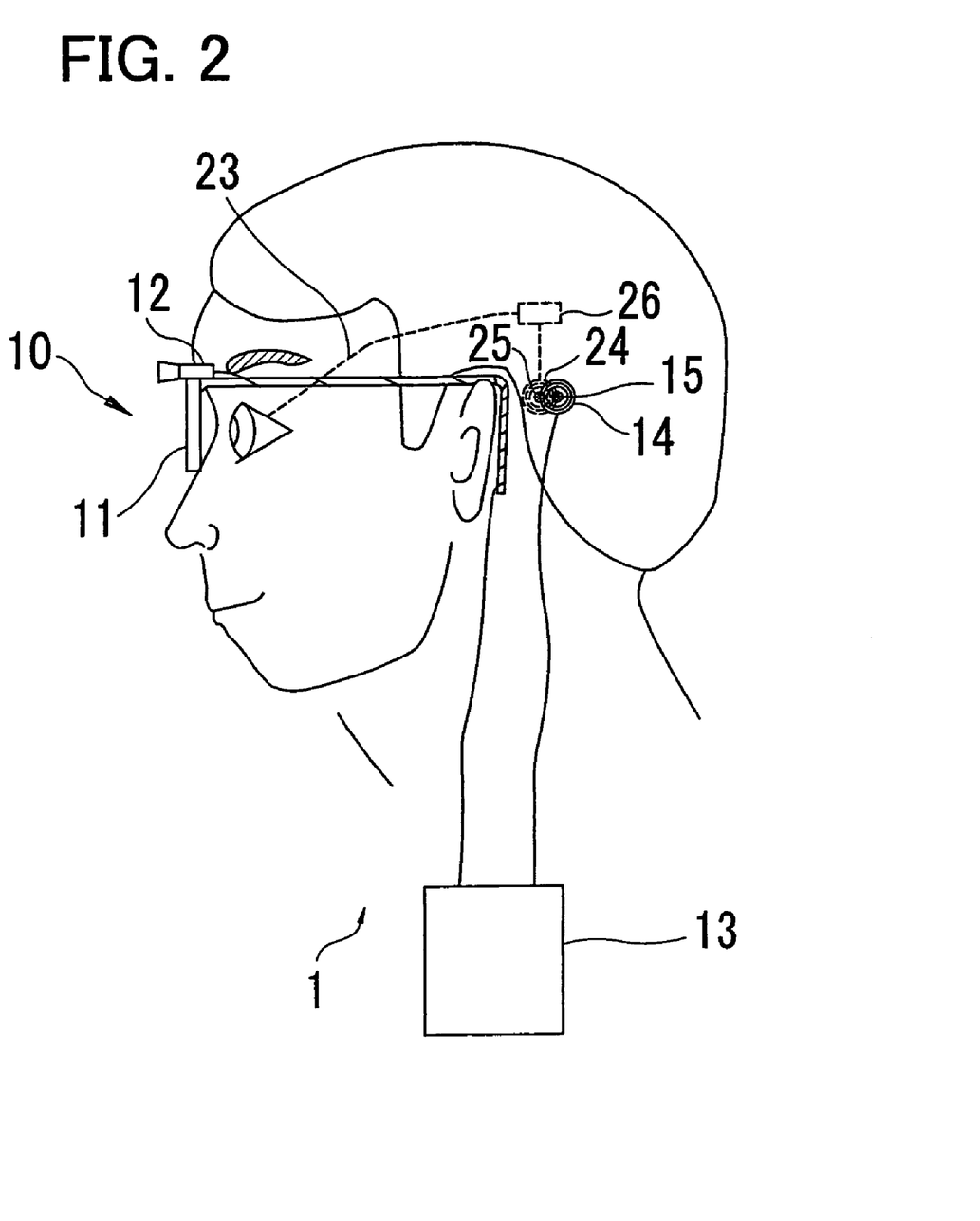
FIG. 2 is a schematic structural view of the visual restoration aiding device.

A detailed description of a preferred embodiment of a visual restoration aiding device embodying the present invention will now be given referring to the accompanying drawings. FIGS. 1 and 2 are schematic views of the visual restoration aiding device in the present embodiment. This device is used in such a way that an electrode array is placed on the outside, of the choroid of a patient's eye to electrically stimulate the cells constituting the retina, thereby inducing the restoration of vision.

The visual restoration aiding device 1 includes an external unit 10 which photographs the outside world, or captures surrounding images, and an internal unit 20 which applies electrical stimulation to the cells constituting the retina to induce the restoration of vision. The external unit 10 includes a visor 11 which a patient puts on, a photographing unit 12 such as a CCD camera which is mounted on the visor 11, an external device 13, and a transmitter (transmission means) 14 including a coil, as shown in FIGS. 1 and 2.

The visor 11 is shaped like eyeglasses, which is put on the front of a patient's eye E. The photographing unit 12 is mounted on the front of the visor 11 and photographs an object to be recognized by the patient.

Figure 4:
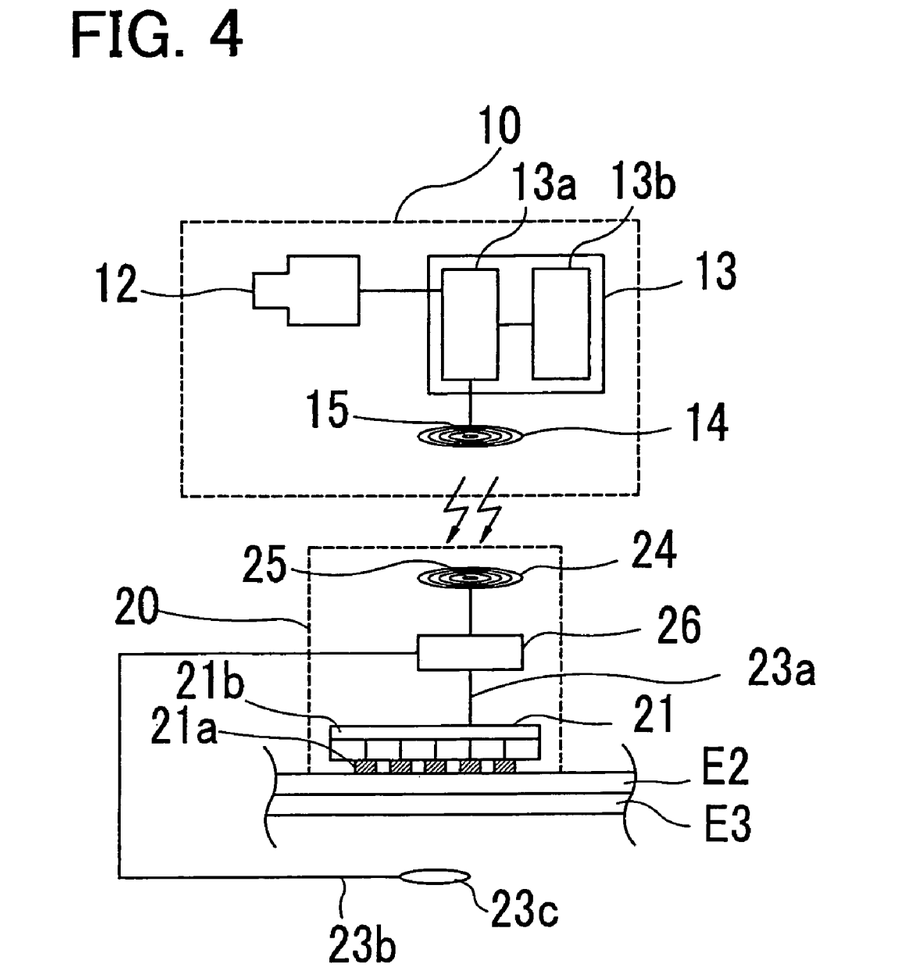
FIG. 4 is a block view showing a control system of the visual restoration aiding device.

The external device 13 includes a signal converter (signal converting means) 13a for converting photograph data taken by the photographing unit 12 into data for electrical stimulation pulse signals and a battery 13b for power supply to the visual restoration aiding device 1 (i.e., the external unit 10 and the internal unit 20), as shown in FIG. 4. The transmitter 14 transmits the pulse signal data converted by the signal converter 13a and electric power for driving the internal unit 20, in the form of electromagnetic waves, to the internal unit 20 by wireless communication. The transmitter 14 is provided at its center with a magnet 15. This magnet 15 is used to enhance the transmitting efficiency by the transmitter 14 and also to fit position of the transmitter 14 to a receiver (receiving means) 24 mentioned later.

The internal unit 20 includes a substrate 21 disposed on the outside of a choroid E2 (namely, between a sclera E1 and the choroid E2), a cable 23, the receiver 24 including a coil and used for receiving electromagnetic waves from the external unit 10, and an internal device 26.

As with the transmitter 14, the receiver 24 is provided at its center with a magnet 25. This receiver 24 is embedded under the skin of the temporal region of the patient's head. Since the magnet 15 is also incorporated in the transmitter 14, the transmitter 14 and the receiver 24 magnetically attract each other when the transmitter 14 is put on the receiver 24 embedded in the head, so that the transmitter 14 is held in place on the temporal region.

The internal device 26 has a conversion circuit which converts the pulse signal data received by the receiver 24 into electrical stimulation pulse signals for inducing the restoration of vision. This conversion circuit processes the pulse signal data and then transmits the electrical stimulation pulse signals to the substrate 21 through the cable 23. The internal device 26 obtains electric power from the electric power signal received by the receiver 24. It is to be noted that the internal device 26 is embedded, as with the receiver 24, in the temporal region of the patient's head.

The cable 23 includes electric wires 23a and 23b each covered by an insulating material with high biocompatibility, the wires being bundled up as one. The cable 23 is embedded, as shown in FIGS. 1 and 2, in such a way as to extend from the internal device 26 toward the eye E along the temporal region under the skin and pass along the inner surface of the upper lid into the orbit. The cable 23 inserted in the orbit is divided into the wire 23a and the other wire 23b as shown in FIG. 1. The wire 23a is placed passing along the outside or inside of the sclera E1 and is connected to the substrate 21. The other wire 23b is placed piercing the pars plana of ciliary body from the outside into the inside of the eye E (i.e. the vitreous body). At this time, a tip portion 23c of the wire 23b is positioned in the eye E so as to face to the substrate 21 in a state where the retina E3 lies between the tip portion 23c and the substrate 21. The tip portion of 23c the wire 23b is not covered to serve as an indifferent electrode.

Although the tip portion 23c of the wire 23b is shaped like a ring in FIG. 1 in order to efficiently function as the indifferent electrode, it is not limited thereto. The shape of the tip portion 23c may be different from the ring, for example, a simple linear shape. In the present embodiment, the tip portion 23c of the wire 23b is used as the indifferent electrode as mentioned above; alternatively, an indifferent electrode may be provided separately from and joined with the wire 23b.

It is to be noted that the indifferent electrode is made of a material generally usable for an electrode, for example, gold, silver, platinum, or the like. The wire 23b is inserted in the eye E by piercing the pars plana of ciliary body from outside the eye E, so that bleeding and retinal detachment can be prevented. Such cable 23 (wires 23a and 23b) is preferably placed under a conjunctiva, a sclera, a skin, and others to prevent infection.

Figure 3A:
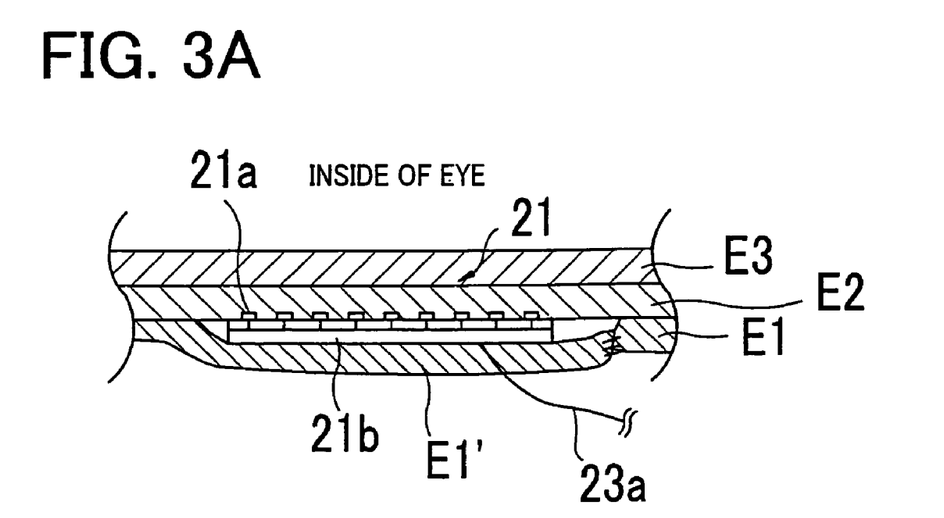
FIG. 3A is a partial sectional view schematically showing a substrate.

FIG. 3A is a view showing a state where the substrate 21 is implanted in the eye E. The substrate 21 is provided with a plurality of electrodes 21a which apply electrical stimulation to the cells constituting the retina E3 and an electric circuit 21b for transmitting an electrical stimulation pulse signal transmitted through the wire 23a to each electrode 23a. Thus, an electrode array is formed, The electrodes 21a may be made of a material generally usable for an electrode, for example, gold, silver, platinum, or the like.

In the present embodiment, each electrode 21a is a positive (+) electrode and the indifferent electrode is a negative (−) electrode. Alternatively, respective polarities may be reversed.

As shown in FIG. 3A, the substrate 21 (electrode array) is placed between the sclera E1 and the choroid E2 while bringing the electrodes 21a into contact with the choroid E2. This placement of the substrate 21 is performed by incising a part of the sclera E1 to form a sclerotic flap E1', placing the substrate 21 on the inside of this sclerotic flap E1 (namely, the outside of the choroid E2), and then closing the flap E1' and stitching up together the incision.

As above, the substrate 21 is held between the sciera E1 and the choroid E2 by stitching up the sclerotic flap E1' in the present embodiment. Alternatively, the substrate 21 may be placed with a tack, a biocompatible adhesive, or the like. The formation of such sclerotic flap E1' and the placement of the substrate 21 may be performed by a well known technique such as sclerotic fenestration in a sclerotic flap producing technique which is used in a filtering operation for glaucoma.

Figure 3B:
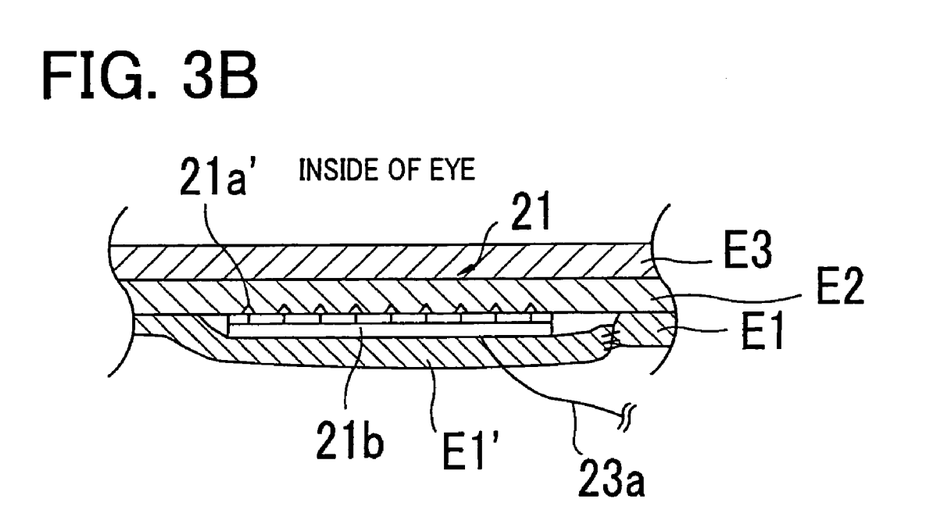
FIG. 3B is a partial sectional view schematically showing another substrate.

The electrodes 21a in FIG. 3A arc flat electrodes having flat surfaces to be brought into contact with the choroid E2. Instead, the electrodes 21a may be formed as notch shaped electrodes 21a' being triangular in cross section as shown in FIG. 3B to slightly press the choroid E2 from the outside thereof.

The intensity of the electrical stimulation from the electrodes 21a is determined as follows. If the electric current is below 20 µA, it is difficult to stimulate the cells constituting the retina E3 such as retinal ganglion cells. If the electric current exceeds 200 µA, on the other hand, the current may damage to the living body. Accordingly, the electric current is preferably determined in a range of from 20 µA to 200 µA, more preferably, from 40 µA to 150 µA.

The duration of application of the electric current is determined as follows. If the duration is below 0.1 ms, the stimulation time is too short to obtain vision. If the duration exceeds 5 ms, on the other hand, the stimulation time is too long, which may damage the living body. Accordingly, the duration is preferably determined in a range of from 0.1 me to 5 ms, more preferably, from 0.1 ma to 1 ms. The waveform of a pulse may be either a monophasic wave or a biphasic wave. Preferably, the biphasic wave is used to enhance the efficiency of electrical stimulation.

In the internal unit 20 constructed as above, the constituent elements except for the electrodes 21a and the indifferent electrode (the tip portion 23c of the wire 23b) are covered by coating agent having a good biocompatibility.

In the visual restoration aiding device having the above structure, the operation for visual restoration is explained referring to a block diagram of a control system in FIG. 4.

Photograph data of an object photographed by the photographing unit 12 is converted into a signal (data for electrical stimulation pulse signal) in a predetermined frequency band by the signal converter 13a, and transmitted by the transmitter 14 to the internal, unit 20 in an electromagnetic wave form. Simultaneously, the signal converter 13a converts electric power supplied from the battery 13b into a signal (electric power signal) having a band different from that of the above mentioned signal (pulse signal data), and transmits the signal in an electromagnetic wave form to the internal unit 20.

The internal unit 20 receives the data for pulse signal and the electric power signal transmitted from the external unit 10 to the receiver 24, and transmits the signals to the internal device 26. This internal device 26 extracts a signal of a band used for the pulse signal data. Based on the extracted pulse signal data, the device 26 forms an electrical stimulation pulse signal to be output from each electrode 21a and transmits the signal to the substrate 21. The device 26 also obtains electric power deriving from the electric power signal received by the receiver 24, the power being to be used for driving the internal unit 20.

Upon receipt of the electrical stimulation pulse signal, the substrate 21 outputs the signal from each electrode 21a through the electric circuit 21b. At this time, the indifferent electrode (the tip portion 23c of the electric wire 23b) is placed within the eye, facing to the electrodes 21a in a state where the retina E3 lies between the indifferent electrode and the electrodes 21a. Accordingly, the electric current output from each electrode 21a flows through the choroid E2 and the retina E3, thus efficiently stimulating the cells constituting the retina E3 such as bipolar cells, retinal ganglion cells, and others. When the cells of the retina E3 are electrically stimulated, the patient recognizes the object photographed by the photographing unit 12 by the effect of electrical stimulation.

The conventional visual restoration aiding device for performing visual restoration by electrically stimulating the cells constituting a retina is constructed such that the electrode array having a plurality of electrodes is placed on the inside or outside of the retina. In this case, a new technique must be established. On the other hand, in the case where the electrode array is placed on the outside of the choroid as in the present embodiment, there is no need to establish a new technique and a burden on the patient is less.

Moreover, in the case where the electrode array is placed on the inside or outside of the retina, the electrode array has to be as small as possible in order to minimize damage to the retina and others. In the present embodiment, on the other hand, where the electrode array is placed on the outside of the choroid, the electrode array will not directly contact with the retina and the portions around it, preventing the damage to the retina. Consequently a larger electrode array can be used as compared with the case where the electrode array is placed on the inside or outside of the retina, so that a larger visual field can be obtained.

Next, some examples of animal experiments are shown below as concrete examples to stimulate the cells constituting the retina by electrical stimulation pulses from the electrode array placed on the outside of the choroid.

The first experiment was performed on normal rats to establish whether an evoked potential occurred or not in a visual center (superior colliculus) when the electrical stimulation was conducted from the outside of a choroid.

<Experiment 1>

As experimental animals, Hooded rats (Long Evans, female, 12-weeks old) having normal pigmented retina were used. All the operations and electrophysiologic records were made under urethane anesthesia (1.75 g/kg, i.p.). During the experiment, electrocardiograms were recorded and disposable pocket body warmers were put on the abdomens of the animals to prevent the decrease of body temperatures.

[Electrical Stimulation]

The sclera fenestration operation was performed on each rat in a size of about 1 mm square at a distance of 1.5 to 2.5 mm from the optic nerve. In the fenestra portion, a silver ball stimulating electrode (0.7 mm in diameter) was placed in contact with the outside of the choroid, and the surrounding area of the electrode was filled with mineral oil to insulate the electrode. An epoxy-coated stainless-steel wire (0.2 mm in diameter) having an uncoated tip portion of about 2 mm in length was used as the indifferent electrode and penetrated from the pars plana of ciliary body into the vitreous body. A constant current stimulus in the form of single-phase rectangular waves of 0.5 ms was applied to between those two electrodes. The polarities of the constant current stimulus were set such that the indifferent electrode was a negative electrode and the stimulation electrode was a positive electrode. The current intensity was set at 154 μA.

[Electrophysiologic Records]

After the head of each rat was stereotactically fixed, the head was incised and a cranial bone in the back part of the right temporal bone was removed. Then, the cerebral cortex was sucked and removed, exposing the dorsal surface of the right superior colliculus. A recording electrode was placed on the cortex of the exposed portion of the superior colliculus and then the surrounding area of the electrode was filled with mineral oil. As the recording electrode, a silver ball electrode (0.7 mm in diameter) was used. A screw type electrode made of stainless steel was embedded as a reference electrode in the occipital bone at a portion closer to the tail by about 1–2 mm from the lambdoid suture. Changes in the electric potential measured (recorded) by use of the recording electrode according to unipolar leads were amplified (an amplification factor: about a ten thousand magnification) by use of a band-pass filter for frequencies of 3 Hz to 3 kHz, and averaging of twenty evoked responses was performed by a signal processor.

Figure 5:
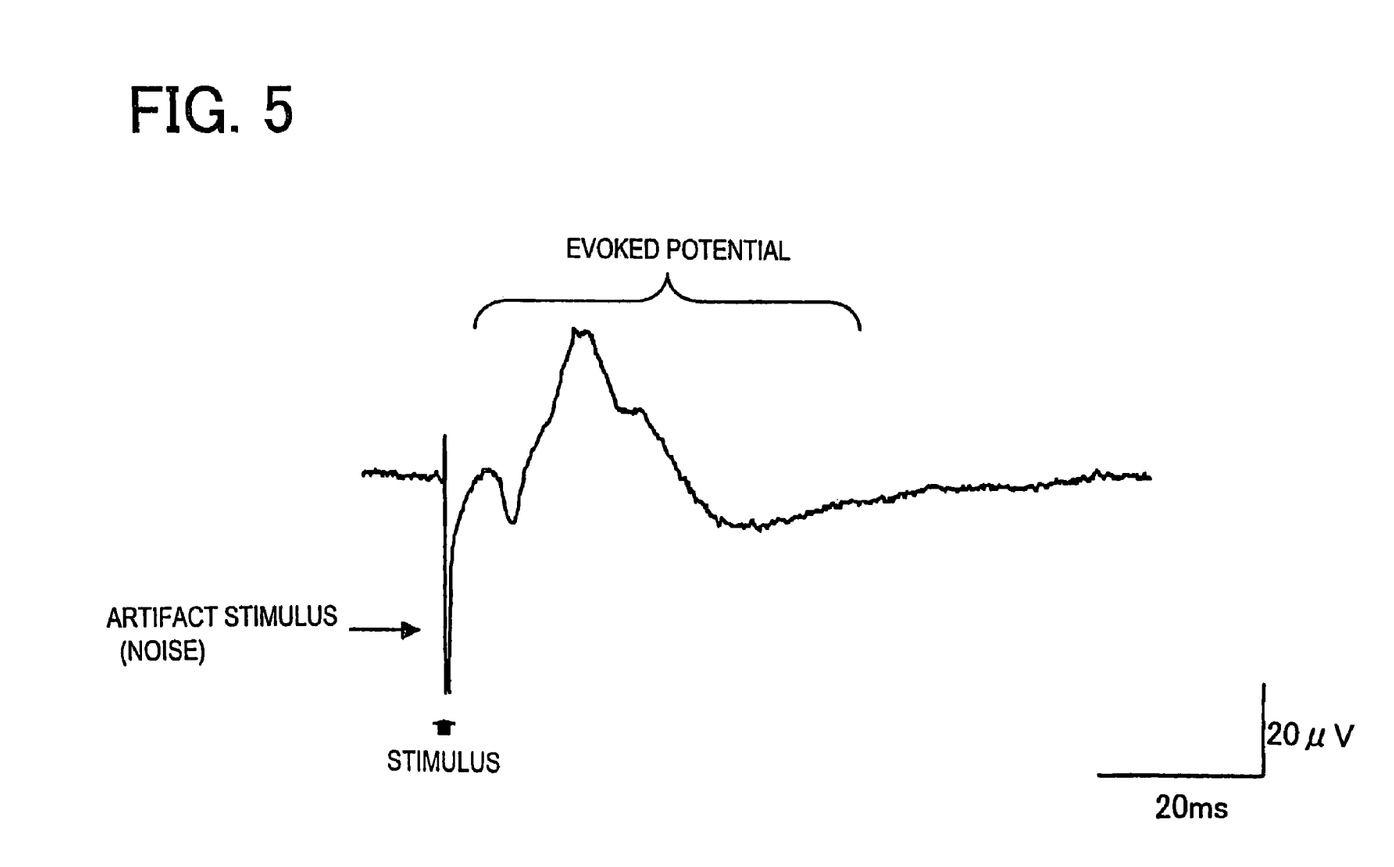
FIG. 5 is a graph showing an evoked potential that occurred in superior colliculus by electrical stimulation to a normal retina of a rat.

The experiment was conducted under the above conditions. The result of the experiment was shown in FIG. 5. As shown in FIG. 5, it was proven that the evoked potential occurred in the superior colliculus.

<Experiment 2>

In the experiment 2, differently from the experiment 1, the experimental animals were RCS rats (Long Evans, male, 25-weeks old) which were used as pigmentosa disease models to examine whether evoked potential occurred or not. The placement of the electrodes for electrical stimulation and the electrophysiologic records were made in the same manner as in the experiment 1. The intensity of electric current was set at six conditions of 15 μA, 20 μA, 30 μA, 40 μA, 30 μA, and 100 μA.

Figure 6:
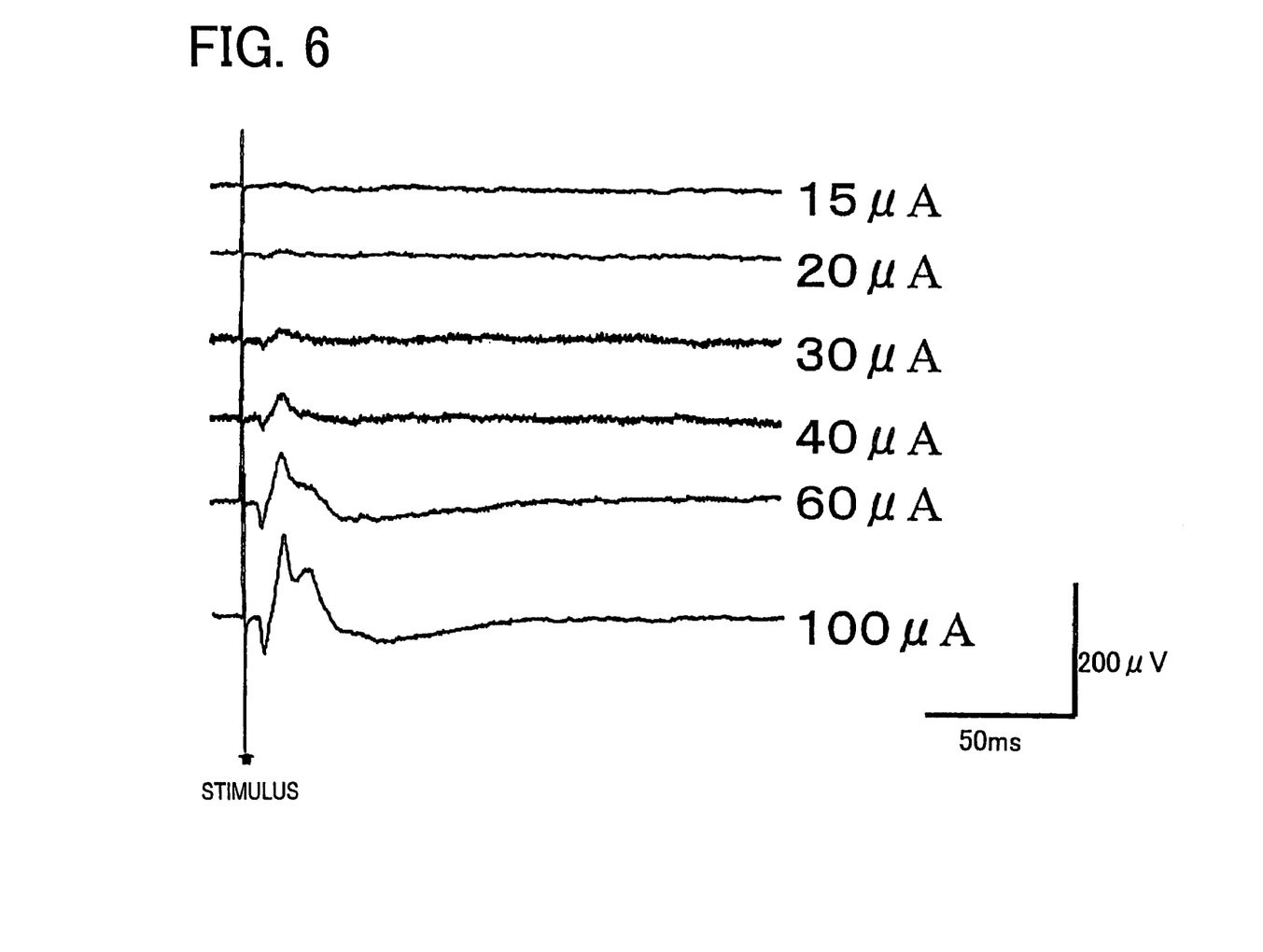
FIG. 6 is a graph showing an evoked potential that occurred in superior colliculus by electrical stimulation to a retina of an RCS rat.

The experiment was carried out under the above conditions. The result thereof was shown in FIG. 6. As seen in FIG. 6, the result shows that the evoked potential occurred in the superior colliculus. As illustrated, the stimulation threshold value of the evoked potential was the current intensity of 20 μA to 30 μA. In the case of 40 μA, the evoked potential had a peak. In the case of 100 μA, all waves completely appeared.

<Experiment 3>

In the experiment 3, it was checked whether the evoked potential that occurred in the experiments 1 and 2 resulted from excitation of the retinal constituent cells. The identical animals as those in the experiment 2 (RCS rats, male, 25-weeks old) were used.

Figure 7A:
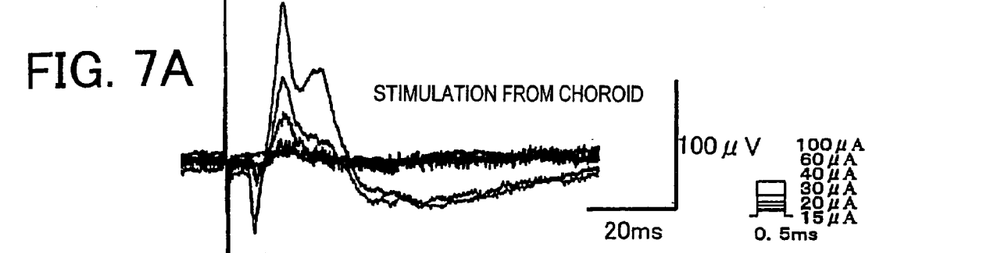
FIGS. 7A and 7B are graphs showing an evoked potential by electrical stimulation to a retina and that by electrical stimulation to an optic nerve for comparison therebetween.
Figure 7B:
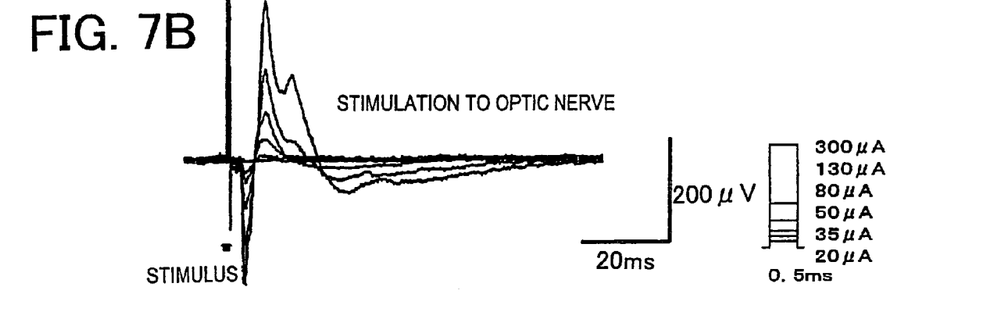

The stimulation was performed in a state where a silver ball stimulating electrode was placed in direct contact with the optic nerve. The placement of an indifferent electrode and an electrode for electrophysiologic records was performed in the same manner and position as in the experiments 1 and 2. The current intensity was equal to that in the experiment 2. The results of the experiment 3 are shown in FIGS. 7A and 7B. FIG. 7A shows the result of the experiment 2 and FIG. 7B shows the result related to the evoked potential by the electrical stimulation to the optic nerve in the experiment 3. The evoked potential with the waveforms (FIG. 7B) similar to those in the experiment 2(FIG. 7A) was observed. The latency period was earlier than in the experiment 2 by 2 Ms to 3 ms.

Judging from the results of the experiment 3, it could be considered that the excitation was transmitted to the superior colliculus through the same pathway in both cases of the stimulation from the outside of the choroid and the stimulation to the optic nerve. This shows that, when the electrical stimulation is performed under the condition that the electrode is placed on the outside of the choroid, the retinal constituent cells are excited by the electrical stimulation and that excitation is transmitted to the superior colliculus through the optic nerve.

From the results of the experiments 1, 2, and 3, it was confirmed that, even where the electrical stimulation was conducted on the retinal constituent cells under the condition that the stimulation electrode was placed on the outside of the choroid, the cells were stimulated and the excitation thereof was transmitted to the superior colliculus.

According to the present invention, as described above, an electrode is placed on the outside of the choroid, so that the damage to the retina can be prevented and an efficient artificial vision can be obtained. An operation can also be performed safely. Since the electrode is placed on the outside of the choroid, additionally, the position of the electrode can easily be changed and a larger electrode array can also be used.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An electrical stimulation method for restoring vision of a patient's eye, comprising the steps of:
    placing a receiver at a position under a skin of a temporal region of a patient's head away from the patient's eye, the receiver being adapted to receive data for electrical stimulation pulse signals based on photograph data taken by a photographing unit outside the patient's eye;
    placing a converter at a position under the skin of the temporal region of the patient's head away from the patient's eye, the converter being adapted to be connected to the receiver and to convert the received data for electrical stimulation pulse signals to electrical stimulation pulse signals;
    placing an electrode array in a sclerotic flap formed by partially incising a sclera of the patient's eye, the electrode array including a plurality of stimulation electrodes being adapted to give the converted electrical stimulation pulse signals to cells constituting a retina of the patient's eye and an electrical circuit connected to the stimulation electrodes to have each electrode output the electrical stimulation pulse signal, the electrode array being provided separately from the converter and connected to the converter through a cable, and closing the sclerotic flap to place the stimulation electrode between a choroid and the sclera;
    placing an indifferent electrode in the patient's eye by piercing the eye from outside, the indifferent electrode comprising a wire that is extended from the converter and covered by an insulating material excepting a distal end and having an opposite polarity to that of the stimulation electrode; and
    outputting the converted electrical stimulation pulse signals having current intensity enough to pass through the choroid and the retina from the stimulation electrodes toward the indifferent electrode to electrically stimulate the cells constituting the retina from a choroid side.

2. An electrical stimulation method for restoring vision of a patient's eye, comprising the steps of:
    placing a receiver at a position under a skin of a temporal region of a patient's head away from the patient's eye, the receiver being adapted to receive data for electrical stimulation pulse signals based on photograph data taken by a photographing unit outside the patient's eye;
    placing a converter at a position under the skin of the temporal region of the patient's head away from the patient's eye, the converter being adapted to be connected to the receiver and to convert the received data for electrical stimulation pulse signals to electrical stimulation pulse signals;
    placing an electrode array in a sclerotic flap formed by partially incising a sclera of the patient's eye, the electrode array including a plurality of stimulation electrodes being adapted to give the converted electrical stimulation pulse signals to cells constituting a retina of the patient's eye and an electric circuit connected to the stimulation electrodes to have each electrode output the electrical stimulation pulse signal, the electrode array being provided separately from the converter and connected to the converter through a cable, and closing the sclerotic flap to place the stimulation electrodes in the sclerotic flap;
    placing an indifferent electrode in the patient's eye by piercing the eye from outside, the indifferent electrode comprising a wire that is extended from the converter and convered by an insulating material excepting a distal end and having an opposite polarity to that of the stimulation electrodes; and
    outputting the converted electrical stimulation pulse signals having current intensity enough to pass through the choroid and the retina from the stimulation electrodes toward the indifferent electrode to electrically stimulate the cells constituting the retina from a choroid side.

* * * * *